United States Patent [19]

Sutcu et al.

[11] Patent Number: 5,810,805
[45] Date of Patent: Sep. 22, 1998

[54] BIPOLAR SURGICAL DEVICES AND SURGICAL METHODS

[75] Inventors: Maz Sutcu, New Hartford; John S. Gentelia, Madison, both of N.Y.

[73] Assignee: ConMed Corporation, Utica, N.Y.

[21] Appl. No.: 598,808

[22] Filed: Feb. 9, 1996

[51] Int. Cl.$^6$ ................................................. A61B 17/36
[52] U.S. Cl. ................... 606/45; 606/51; 606/52
[58] Field of Search .................. 606/41, 42, 45–52, 606/170, 171, 174, 180, 205–208

[56] References Cited

U.S. PATENT DOCUMENTS

| | | | |
|---|---|---|---|
| 856,927 | 6/1907 | Straw | 606/174 |
| 1,916,722 | 7/1933 | Ende | 606/50 |
| 4,433,687 | 2/1984 | Burke et al. . | |
| 4,499,899 | 2/1985 | Lyons, III . | |
| 4,590,936 | 5/1986 | Straub et al. | 606/174 |
| 4,655,216 | 4/1987 | Tischer . | |
| 4,770,174 | 9/1988 | Luckman et al. . | |
| 5,030,206 | 7/1991 | Lander . | |
| 5,123,904 | 6/1992 | Shimomura et al. . | |
| 5,174,300 | 12/1992 | Bales et al. . | |
| 5,267,998 | 12/1993 | Hagen . | |
| 5,269,780 | 12/1993 | Roos | 606/42 |
| 5,269,782 | 12/1993 | Sutter . | |
| 5,281,220 | 1/1994 | Blake, III . | |
| 5,366,468 | 11/1994 | Fucci et al. . | |
| 5,383,888 | 1/1995 | Zvenyatsky et al. . | |
| 5,445,638 | 8/1995 | Rydell . | |
| 5,472,442 | 12/1995 | Klicek | 606/48 |
| 5,480,409 | 1/1996 | Riza . | |
| 5,499,992 | 3/1996 | Meade et al. . | |
| 5,522,830 | 6/1996 | Aranyi . | |

*Primary Examiner*—Michael Peffley
*Attorney, Agent, or Firm*—Larson & Taylor

[57] ABSTRACT

A surgical device includes a pair of end effector members. Rotation of one or both of the members about the longitudinal axis thereof enables a section of tissues to be inserted between the members and then grasped and compressed thereby. In use in laparoscopy, the members are rotated (or biased) to the closed position to enable insertion of the members through a cannula, and, once inside the patient, the members are rotated from the closed position so that tissue can be inserted therebetween for gripping purposes. Electrosurgical current is applied to the members to provide coagulation of tissue held between the members. By simply rotating the rotating member between two opposed positions, coagulation can be carried out at two spaced zones. A third cutting member may then be used to cut the tissue along a midline between the coagulation zones. In another embodiment, a cutting edge on the rotating member is rotated into position to cut tissue after a further, blunt edge of the rotating member has been positioned relative to the fixed member to provide coagulation.

45 Claims, 7 Drawing Sheets

FIG. 1
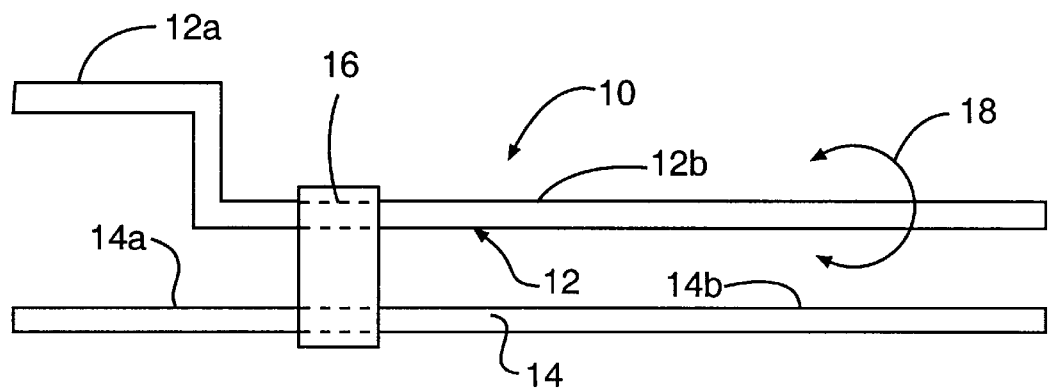
FIG. 2
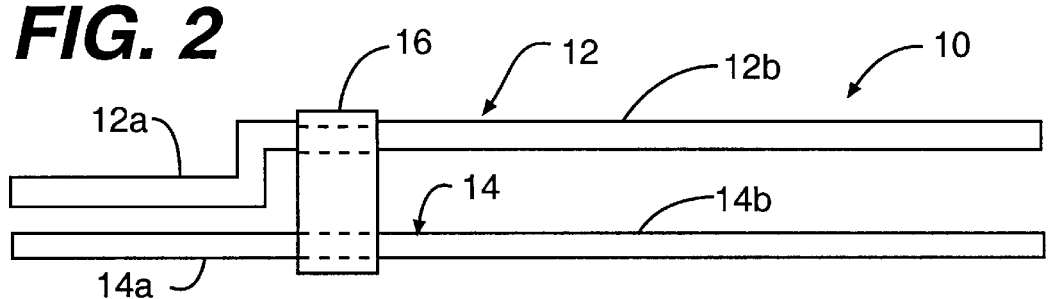
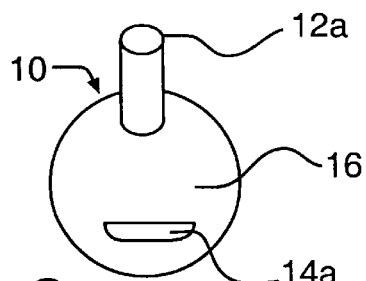
FIG. 3
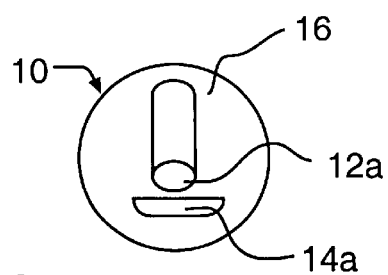
FIG. 4

BIPOLAR SURGICAL DEVICES AND SURGICAL METHODS

BACKGROUND OF THE INVENTION

1. Field of the Invention

The present invention relates to bipolar electrosurgical devices such as electrosurgical scissors, gaspers and the like which include end effectors for effecting cutting, coagulation and other functions.

2. The Prior Art

Although there are many different types and forms of prior art electrosurgical grasping and scissors devices, it is characteristic of these devices that they typically employ a pivoting arrangement including a common pivot pin about which both of the end effectors pivot, so as to produce rotatory movement about an axis perpendicular to the cutting plane. The fact that both members pivot about a common axis creates a problem when the two members must be electrically insulated as is required, e.g., in electrosurgical applications.

There are, of course, many patents relating to electrosurgical scissors, graspers and like devices. Some of these devices provide both coagulation and cutting. Patents of interest in the field include the following: U.S. Pat No. 5,269,780 (Roos), U.S. Pat No. 5,267,998 (Hagen), U.S. Pat No. 5,269,782 (Sutter), U.S. Pat No. 5,445,638 (Rydell et al.), and U.S. Pat No. 4,655,216 (Tischer). Briefly considering these patents, the Roos patent discloses a bipolar electrosurgical device which includes three mutually insulated contact rods for cutting and coagulation. The Hagen patent discloses a bipolar electrosurgical device with two stationary coagulation electrodes and a movable cutting electrode. The Sutter patent discloses a bipolar electrosurgical device including two elongated electrodes. The Rydell et al. patent discloses a bipolar electrosurgical device including electrode forceps jaws and a movable cutter between these jaws. The Tischer et al. patent discloses a bipolar electrosurgical device for coagulating an area and cutting tissue in the coagulated area.

SUMMARY OF THE INVENTION

Generally speaking, the present invention relates to a surgical device including end effector members, one or more of which is rotated into position along the longitudinal axis of the device so as to contact and retain tissue between the members. This results in significant advantages with respect to simplicity of design and ease of manufacturing as will appear from the discussion below. In this regard, it will be appreciated that difficulties associated with the pivot pin constructions of the prior art are reduced significantly by pivoting the electrode members independently of each other. The rotational axis of each electrode member of the invention lies in the cutting plane, as opposed to the transverse plane as in the prior art. Because separate pivoting is provided, the construction can be simplified and there is no need for bushings for electrical insulation nor rivets. The small rivets associated with prior art constructions present problems in manufacture and assembly, because accurate positioning using specially designed fixtures is necessary to control the loads and deformations created during flaring of the ends of the rivets, thereby adding to manufacturing costs. As will appear, there is no need for bushings with the present invention because the support structure is made from an insulating material.

In accordance with one aspect of the invention, a bipolar electrosurgical device is provided which comprises an end effector including first and second elongate electrode members supported in spaced relation one beside the other; means for applying electrosurgical power to the electrode members; and means for rotating at least the first electrode member about the longitudinal axis thereof so as to vary the spacing between at least distal end portions of said first and second electrode members.

preferably, the distal end portion of the first electrode member comprises an offset portion the spacing of which from the second electrode member is variable responsive to rotation of said electrode member about the longitudinal axis thereof. Advantageously, this offset portion includes a portion which extends parallel to an opposed portion of the distal end of the second electrode.

In a preferred embodiment, the electrode members include portions supported in spaced parallel relation and the first electrode member includes a further, offset portion at the distal end thereof. Advantageously, as above, the offset portion includes an end portion which extends parallel to an opposed portion of said second electrode.

preferably, the device further comprises an electrically insulating spacer and support element having spaced openings therethrough through which the electrode members extend. In an advantageous implementation, these openings have parallel longitudinal axes.

In one preferred embodiment, the end portion of the first electrode member is rounded in cross section. In one advantageously implementation of this embodiment, the distal end portion of the first electrode member is substantially circular in cross section. In one preferred embodiment, the second electrode member has a substantially planar profile in cross section.

In an embodiment of the invention wherein the surgical device can be used for cutting, the distal end portion of the first electrode member includes a cutting edge. In this embodiment, the distal end portion preferably further includes a blunt edge substantially opposite the cutting edge.

In accordance with another aspect of the invention, at least one of the electrode members is movable axially along the longitudinal axis thereof out of registration with the other of the electrode members so as to expose one of the electrode members for use as a monopolar cutting element.

In another preferred embodiment, the distal end portions of both of the electrode members each include a cutting edges so as to provide a scissors.

Advantageously, the second electrode member is stationary and the end portion thereof comprises a blade formed from part of a cylinder inclined towards the distal end thereof and including the cutting edge for the second member, the distal end portion of said the first electrode member comprising a blade formed from part of a cylinder, and including the cutting edge for the first member, and the rotation means including means for rotating the first electrode member about an offset axis such that the cutting edges of the blades contact each other along a narrow line of contact.

Advantageously, either or both of the electrode members includes a hook at the distal end thereof for preventing tissue held on the electrode members from sliding off therefrom.

In a further preferred embodiment which also provides cutting, the device further comprises a further, cutting member for cutting tissue held by the electrode members.

In an embodiment providing both coagulation and cutting, the first electrode member is rotatable to provide coagulation of tissue held between the electrode members at two spaced coagulation zones when electrosurgical power is applied to the electrode members, and the device further comprises a further cutting member disposed relative to the electrode members so as to effect cutting of tissue held by said electrode members at a zone between the coagulation zones.

In accordance with a further aspect of the invention, a method is provided for coagulating an elongate section of tissue of a patient using a electrosurgical device having an end effector comprising first and second spaced electrodes wherein at least said first electrode is rotatable, the method comprising: placing the elongate section of tissue into a space between said first and second electrodes created by rotating the first, rotatable electrode away from the second electrode; rotating the first, rotatable electrode towards the second electrode so as to engage and hold the tissue between the electrodes at a first location on the tissue; applying electrosurgical current to the electrodes so as to produce a first weld line in the tissue held between the electrodes at the first location; rotating the first rotatable electrode away from the first location so as to engage and hold the tissue between the electrodes at a second location on the tissue; applying electrosurgical current to the electrodes to create a second weld line in the tissue held between the electrodes at the second location; and cutting the tissue between the weld lines.

Preferably, the first, rotatable electrode is rotated to the second location while the second electrode is held fixed. Advantageously, the cutting is carried out by a cutting element forming part of said electrosurgical device.

In accordance with yet another aspect of the invention, an electrosurgical scissors device is provided for carrying out both cutting and coagulation operations, the scissors device comprising: first and second electrode members supported in spaced relation, the first electrode member including a distal end portion and an elongate portion defining a longitudinal axis and the distal end portion of the first electrode member including a cutting edge; means for enabling electrosurgical current to be supplied to the electrode members; and means for rotating the first electrode member about the longitudinal axis thereof so as to vary the spacing between the distal end portion of the first electrode member and a distal end portion of the second electrode so as to provide cutting of tissue positioned between the electrode members with the cutting edge.

Preferably, the distal end portion of the first electrode member includes a surface for, when juxtaposed with an opposing surface of the distal end of said second electrode member, enabling coagulation of tissue positioned between the electrode members in response to electrosurgical current being supplied to the electrode members.

Advantageously, the distal end portion of the first electrode member includes a further, rounded edge opposed to the cutting edge and movable into juxtaposition with the distal end portion of the second electrode to effect coagulation of tissue positioned between the electrode members.

In accordance with an additional aspect of the invention, a method of coagulation and cutting of tissue is provided which uses an electrosurgical device comprising first and second spaced, elongate electrode members wherein the first electrode member is rotatable about the longitudinal axis thereof so as to vary the spacing between a distal end portion thereof and a distal end portion of the second electrode member, and wherein the distal end of the first electrode member includes a cutting edge, said method comprising: positioning tissue to be coagulated and cut into a space between the electrode members; rotating the first electrode member so that a surface of the distal end portion thereof is brought into juxtaposition with an opposed surface of the distal end portion of the second electrode member; applying electrosurgical current to said electrode members to cause coagulation of a portion of the tissue between the electrode members; and further rotating the first electrode member so as to bring the cutting edge thereof into contact with the tissue to provide cutting thereof.

Other features and advantages of the invention will be set forth in, or apparent from, the following detailed description of the preferred embodiment of the invention.

BRIEF DESCRIPTION OF THE DRAWINGS

FIG. 1 is a schematic side elevational view of the end effector portion of a surgical device constructed in accordance with a preferred embodiment of the invention;

FIG. 2 is a side elevational view of the device of FIG. 1 showing the rotatable electrode member in a second position thereof;

FIG. 3 is an end elevational view of the device as shown in FIG. 1;

FIG. 4 is an end elevational view of the device as shown in FIG. 2;

DESCRIPTION OF THE PREFERRED EMBODIMENTS

Figure 5:
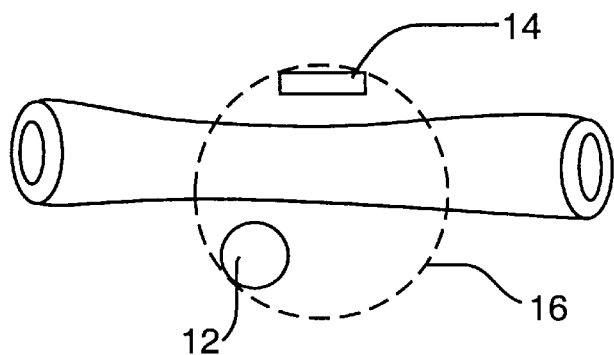
FIGS. 5 to 8 are schematic end views showing steps in a coagulation and cutting method of the invention using a surgical device constructed in accordance with an embodiment similar to that of FIGS. 1 to 4.

Referring to FIGS. 1 to 4, there are shown the key elements of a bipolar surgical device or instrument, generally denoted 10, constructed in accordance with a preferred embodiment of the invention. In this embodiment, device 10 includes a first, movable electrode 12 and second, fixed electrode 14. Electrodes 12 and 14 are mounted in guide holes 16a and 16b provided in an electrically non-conductive guide 16 and supported in generally parallel relation. As illustrated, fixed electrode includes a blade or end portion 14a and a main, shaft portion 14b, while movable electrode 12 includes an end or blade portion 12a in the form of a crank arm or offset arm which is rotatable, by a rotation means or mechanism indicated schematically by double-headed arrow 18, about the longitudinal axis defined by the main, remaining, shaft portion 12b of the electrode 12. As a result, end portion 12a can be rotated between a first position shown in FIGS. 1 and 3 wherein end portion 12a is substantially spaced from fixed electrode 14 and a second position shown in FIGS. 2 and 4 wherein end portion 12a is disposed close to fixed electrode 14. Of course, other, different rotational positions of end portion 12 are also possible, depending on the application.

As illustrated in FIGS. 3 and 4, fixed electrode 14 is substantially flat in cross section, while electrode 12 is substantially round. However, it will be understood that the two electrodes can each have the same round or flat shapes, or can have different shapes, or can have other shapes, depending on the application. Similarly, although guide or support member 16 is, as illustrated, generally cylindrical in shape and includes two spaced, parallel openings 16a and 16b therein through which electrodes 12 and 14 extend, guide members of other shapes as well as other, different guide and support arrangements can also be employed. It is noted that although guide holes 16a and 16b are substantially parallel in the illustrated embodiment, the guide holes can be angled to bias the distal ends of the electrodes 12 and 14 toward or against each other and to thus decrease the cross section of the leading or distal end of the device.

In an alternative embodiment to that illustrated in FIGS. 1 to 4, both of the electrode members 12 and 14 can be rotated. Also, both electrode members can include a plurality of electrodes (not shown) thereon, i.e., at the end region thereof, and these electrodes can be formed by electrically isolated segments. In another implementation, one or more of the electrode members 12 and 14 can be spring loaded by a spring or springs so that the end effector formed thereby is normally in the closed position (FIGS. 2 and 4).

It will be appreciated that in the closed position (or, in the case of a spring biassed implementation, the normally closed position), the surgical device 10 is readily insertable through a cannula (not shown) into the body. Once inside, electrode 12 is rotated by the surgeon by applying a rotational force by means of mechanism 18 to open the space between the end portion 12a of the electrode 12 and the corresponding end position of the fixed electrode 14 so as to engage and/or grasp and compress tissue therebetween.

The end effector of the invention possesses an important advantage over the prior art in that the opposing members, i.e., electrodes 12 and 14, approach each other over the tissue in a parallel manner or fashion. In this regard, one or both of the electrodes 12 and 14 may optionally include a roller (not shown) so that the electrodes glide over the surface of the tissue with minimum resistance so as to reduce the risk of damage to the tissue. Of course, it will be understood that a comparable effect is provided by the rounded or circular cross section electrode 12 which acts in a manner similar to a roller. The operation of device 10 in this regard will perhaps be better understood from the discussion below, in connection with FIGS. 5 to 8, of one use of the device.

Referring to FIG. 5, the device 10 of FIGS. 1 to 4 is shown in an open state with the electrodes 12 and 14 disposed with suitable spacing therebetween (as provided by rotation of electrode 12) so as to permit receipt between the electrodes 12 and 14 of a length or section of tissue T shown here in the form of a tube.

Figure 6:
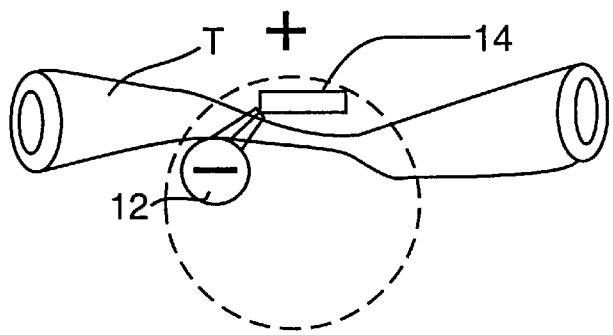

The next step, which is illustrated in FIG. 6, is to rotate electrode 12 so as to compress the tissue T between electrodes 12 and 14. Electrosurgical power is then applied to the electrodes 12 and 14 (which, in this exemplary embodiment, are at negative and positive polarities, respectively, as shown) so as to create a first weld or seam line, at WL1, as illustrated.

Figure 7:
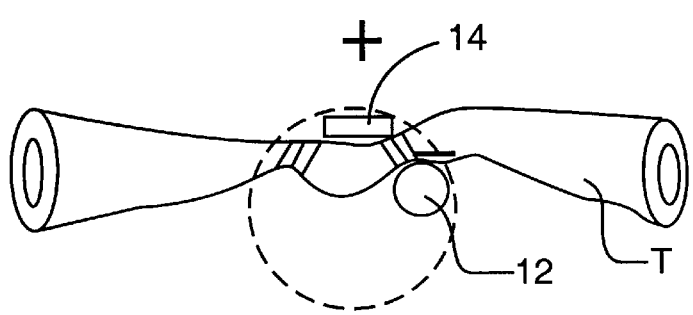

As shown in FIG. 7, the movable electrode 12 is then rotated in the opposite direction to compress the tissue T on the opposite side of fixed or stationary electrode member 14. Electrosurgical power is then applied so as to create a second weld or seam line WL2.

Figure 8:
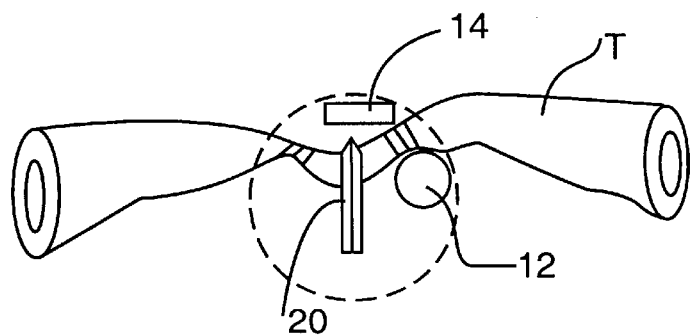

After creating spaced seam lines WL1 and WL2, as a further step, which is illustrated in FIG. 8, an optional linear cutter 20 is used to cut the tissue T in between the two weld lines WL1 and WL2 and thus sever the tissue T at that point. Thus, a cut is made between two coagulated regions or portions of the tissue T and bleeding from the severed portions of the tissue is minimized.

Figure 9:
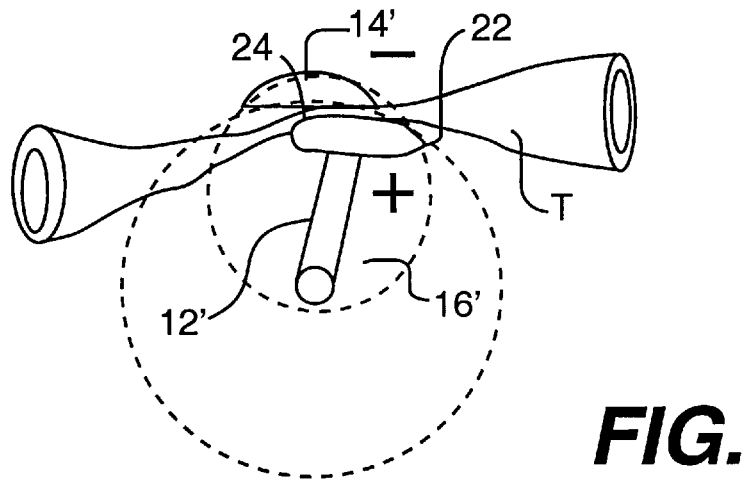
FIGS. 9 and 10 are schematic end elevational views showing steps in a further method of the invention using a surgical device constructed in accordance with a further embodiment of the invention.
Figure 10:
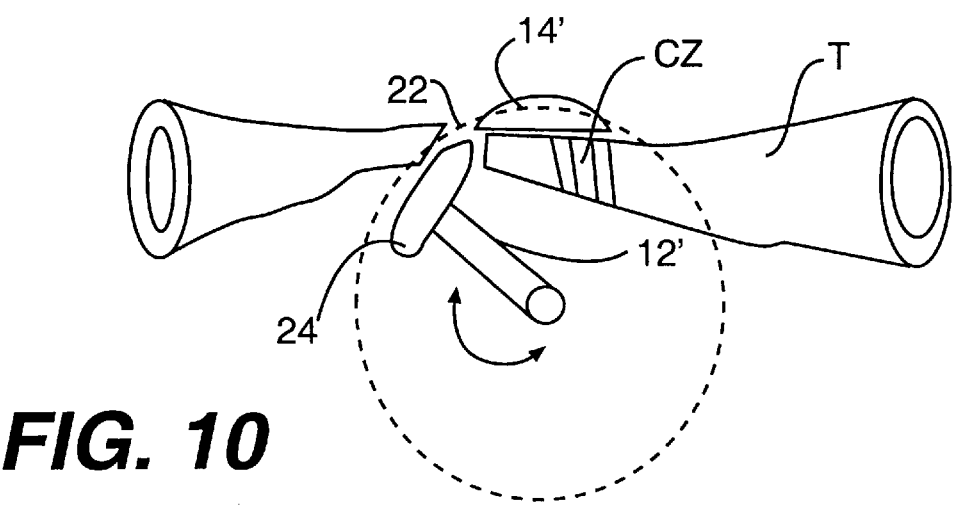

Referring to FIGS. 9 and 10, a further embodiment of the invention is shown wherein the electrodes of the end effector form bipolar scissors. These scissors can be used to provide coagulation and to also cut tissue with a scissors-like action after tissue coagulation. This embodiment is similar to that of FIGS. 1 to 4 and similar or corresponding elements have been given the same reference numerals with primes attached. As illustrated, in this embodiment, the movable electrode or blade 12' includes, at one end of the profile or cross section thereof, a sharp edge 22 for cutting and further includes, at the other end thereof, a blunt edge 24. The cutting edge 22 is preferably angled as shown so that the cutting progresses form proximal to distal. Stationary electrode 14' includes a flat inner surface 26 although, again, other shapes can be employed.

In FIG. 9, the movable electrode or blade 12' is shown in the position thereof for achieving tissue coagulation using the bipolar scissors, i.e., with rotating electrode 12' in generally parallel registration with fixed electrode 14'. The coagulated zone created by applying electrosurgical power to the electrodes 12' and 14' is indicated at CZ in FIG. 10.

FIG. 10 also shows the cutting action of the cutting edge 22. In this regard, after the blunt end 24 of rotating electrode or blade 12' is used for coagulation, the electrode or blade 12' is rotated, as shown, such that the sharp cutting edge 22 engages and cuts the tissue T to the left of coagulated zone CZ as viewed in FIG. 10. It will be appreciated that by slightly moving the electrode 12' and 14' in the transverse plane, the cut plane can be moved to the middle of the coagulated zone CZ.

Figure 11:
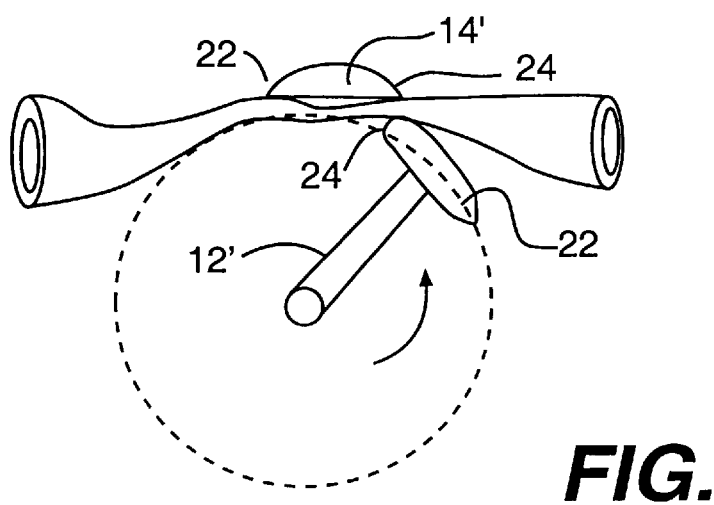
FIG. 11 is a schematic end elevational view similar to that of FIG. 9 illustrating a further implementation of this aspect of the invention.

Referring to FIG. 11, an embodiment is shown which is similar to that of FIGS. 9 and 10 except that the blunt end 24 of the rotating electrode member 14' is rotated to a position wherein this end is disposed adjacent to but does not move under the fixed electrode member 12' as in FIG. 9. Preferably, as illustrated in FIG. 11, the fixed electrode member 12' of this embodiment is of a shape similar to that of the rotating electrode member 14' and thus similarly includes a blunt end 24 and a sharp, cutting end 22. In this embodiment, the rotating electrode member is rotated in a clockwise direction to enable the sharp ends 22 of members 12' and 14' to provide a cutting action and in a counter-clockwise direction to bring the blunt ends 24 into operation to enable a coagulation procedure to be carried out.

Figure 12:
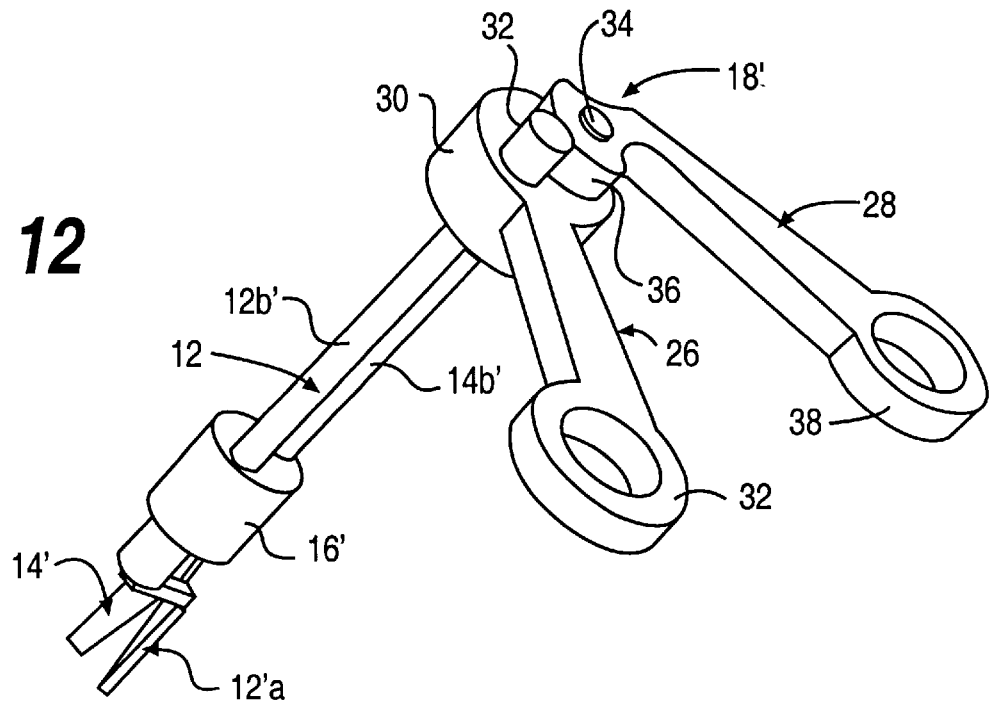
FIG. 12 is a perspective view of a further embodiment of the surgical device of the invention including a preferred implementation of the actuating mechanism.

Referring to FIG. 12, there is shown a scissors instrument which is similar to that illustrated schematically in FIGS. 9 and 10 (and in FIG. 11) and which includes a specific implementation of the actuating mechanism indicated schematically in FIG. 1. The instrument of FIG. 12 includes a rotatable electrode 12' and a fixed electrode 14' of the character described above and including shaft portions 12b' and 14b', respectively, mounted in parallel relation in a guide member 16'. An actuating mechanism, generally denoted 18', includes a pair of scissor arms 26 and 28 which lie in planes generally orthogonal to the axes of electrodes 12' and 14'. Arm 26 includes a flat-sided, generally cylindrical hub or body portion 30 including a pair of spaced openings or apertures (not shown) extending between the flat faces thereof, and a finger grip 32 at the other end of arm 26. The shaft portion 12b' of rotatable electrode 12' extends through one of these openings and terminates in a driven gear 32 of generally cylindrical shape. Similarly, the shaft portion 14b' of fixed electrode 14' extends through the other of these openings and terminates in a stub shaft or mount 34 about which rotates a driving, sector gear 36 formed at the proximal end of arm 28 and disposed so as to mesh with gear 32. A finger grip 38 is formed at the opposite, distal end of arm 28.

It will be appreciated that with the actuation mechanism 18' illustrated in FIG. 12, relative movement of arms 26 and 28, effected by a user gripping finger grips 32 and 38, will cause sector gear 36 to drive driven gear 32 and thus produce controlled rotation of the blade or end portion 12a' of electrode member 12'.

Figure 13:
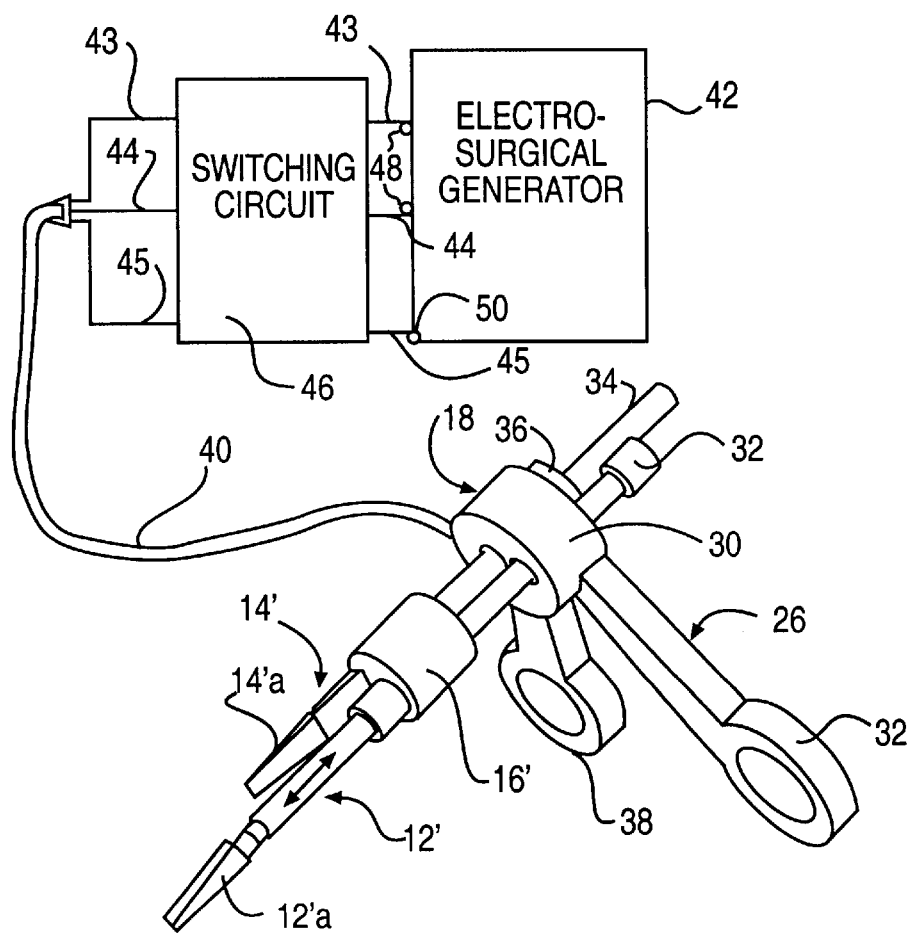
FIG. 13 is a perspective view of a further embodiment of the surgical device shown in FIG. 12.

Referring to FIG. 13, an alternative embodiment of the scissors instrument of FIG. 12 is shown. Apart from an important difference described in more detail below wherein provision is made for axial movement of the electrode members, the embodiment is very similar to that of FIG. 11 and thus the corresponding elements have been given the same reference numerals. In accordance with this aspect of the invention, either of the opposing electrode members 12' and 14', i.e., whether rotating or non-rotary, is slidable along the longitudinal axis of the device so that one of the blades (12a' or 14a') can be used as a scalpel or, in the electrosurgical application shown in FIG. 12, as a monopolar cutting element or cutter, while the other member is held in a retracted position. In the illustrated embodiment, both of the electrode members are shown as being axially movable to emphasize that either can be made to so move although in a practical device, only one would normally be movable. In an example of such a practical implementation, guide and support element 16' would be located inwardly of the position shown in FIG. 12 so as to permit electrode retraction and rotating electrode 12' will be retracted so as to "expose" fixed electrode members 14' for cutting purposes.

Movement of the electrode members 12' and/or 14' can be effected in the illustrated embodiment by simply pulling or drawing on the electrode member in question so that the member slides axially in the corresponding guide opening in the body member or hub 30 of arm 26, using a gripping instrument, such as a pair of pliers, if necessary. If necessary or desired, a separate gripping part or portion (not shown) can be provided at the proximal end of the movable electrode member and a keying or locking mechanism (not shown) can be provided to key or lock the member in place in the normal operating position thereof wherein gears 32 and 34 are in engagement. More generally, it will be appreciated that other different mechanisms for effecting this axial movement of one or more of the electrode members can be employed.

It is noted that the guide or supporting member 16' located near the distal end of the device can be secured to the non-rotating electrode member 14' but this is not necessary. In this regard, the guide member 16' can be constrained to move with the rotating member 12' in the axial direction as indicated in FIG. 13. This allows retracting of the non-rotary member 14', if necessary, as indicated. In any event, the important thing with this aspect of the invention is that at least one of the electrode members is axially moveable to a position wherein the electrode blades 12a' and 14a' are no longer in registration, so that the "exposed" member can be used as a scalpel or a monopolar cutting element.

As a result of the features just described, the device of FIG. 12 can be used as a bipolar electrosurgical cutting device or, with one electrode member exposed, as a monopolar electrosurgical cutting device. In the illustrated embodiment, a cable or other electrical connection 40 which connects an electrosurgical generator or unit (ESU) 42 to the device includes three wires 43, 44 and 45 connected between the handle (actuator) mechanism 18' and the ESU 42 through a switching circuit or network 46. Wires 43 and 44 are connected to the bipolar inputs 48 of ESU 42 while wire 45 is connected to the monopolar input 50. With this arrangement, monopolar or bipolar electrosurgery or a combination of both can be carried out.

Figure 14:
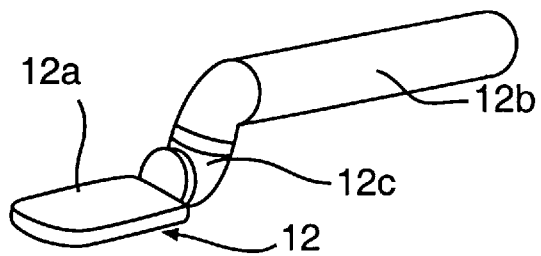
FIG. 14 is a perspective view of a further embodiment of the rotating electrode member of the invention.
Figure 15:
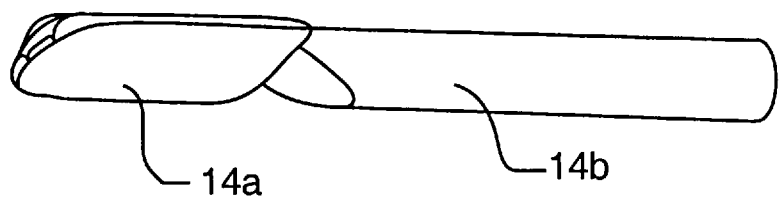
FIG. 15 is a perspective view of a further embodiment of the fixed electrode member of the invention.
Figure 16:
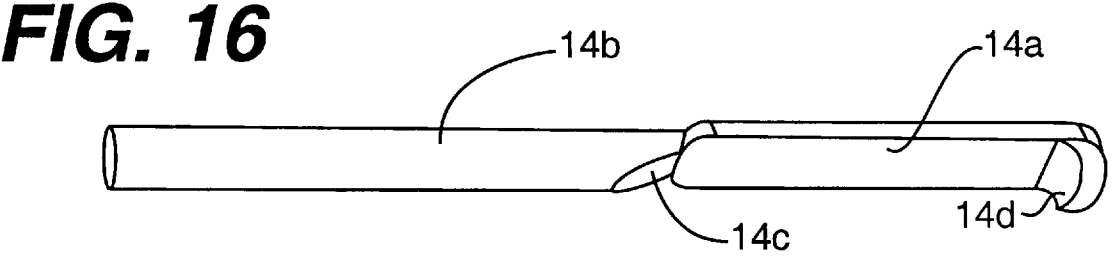
FIG. 16 is a perspective view of yet another embodiment of the fixed electrode member of the invention.

As noted above, the distal ends of the end effectors can have other different and useful shapes depending on the application to which the device is put. A further preferred embodiment of the rotating electrode member 12 is shown in FIG. 14 wherein electrode member 12 includes a flat, shaped distal end portion 12a, a round proximal end portion 12b and a round transition portion 12c. A further preferred embodiment of the fixed electrode member 14 is shown in FIG. 15 wherein electrode member 14 includes a flat, shaped distal end portion 14a and a round proximal end portion 14b including a tapered transitional portion 14c. FIG. 16 also shows a further embodiment of the fixed electrode member 14 including a flat distal portion 14a having a hook 14d at the free end thereof for assisting in retaining in place tissue that has been grasped by the electrode members and thus preventing such tissue from slipping off the end of distal end portion 14a. In this embodiment, the proximal end portion 14b is rounded and includes a transitional portion 14c similar to that of FIG. 15. It will be appreciated that a similar hook can also be provided on the rotatable electrode member for the same purpose.

Figure 17:
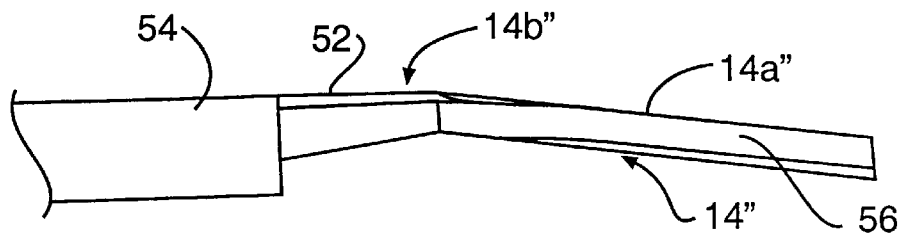
FIGS. 17, 18 and 19 are a side elevational view, a bottom plan view and a front elevational view, respectively, of a further embodiment of the fixed electrode member of the invention.
Figure 18:
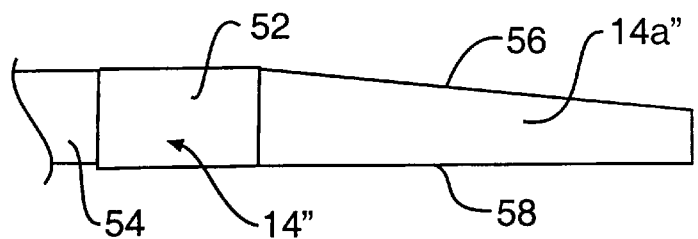
Figure 19:
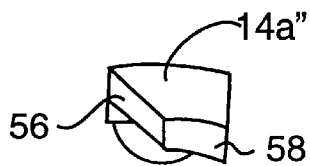

Referring to FIGS. 17 to 19, a further embodiment of the fixed or stationary scissors blade or electrode member is shown. The overall electrode member is similar to that shown in FIGS. 1 to 4 and like elements have been given the same reference numeral with a double prime attached. As illustrated, the blade, which is denoted 14a'', is formed as part of an inclined hollow cylinder, with an inclination from the horizontal of about 7° in an exemplary, non-limiting embodiment. In addition to blade portion 14a'', the remaining, handle portion 14b'' of electrode member 14'' includes a connector element 52 and a cylindrical support portion 54. As best seen in FIG. 18, which is a bottom plan view, blade 14a'', which is tapered as illustrated, includes an inclined cutting edge 56 and an opposed, generally straight edge 56 which is flat or blunt.

Figure 21:
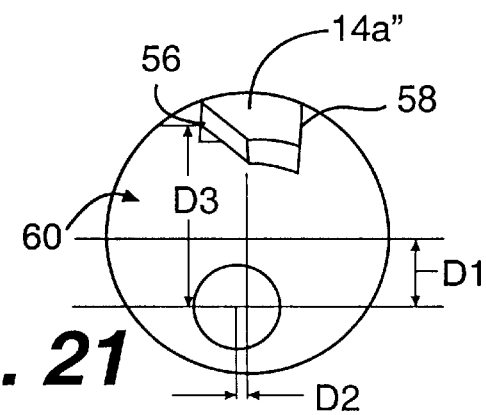
FIGS. 20 and 21 are a side elevational view and a front elevational view respectively, of yet another embodiment of the fixed electrode member.
Figure 20:
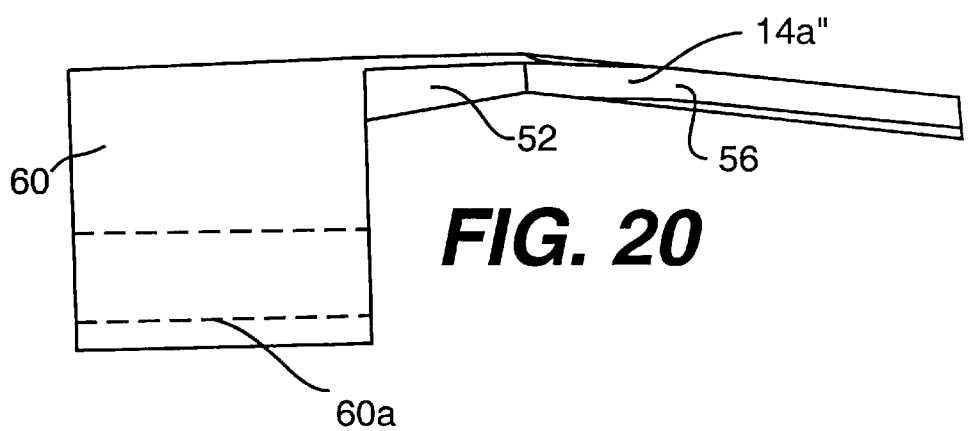

Referring to FIGS. 20 and 21, yet another embodiment of the fixed or stationary scissor blade is shown. This embodiment is very similar to that of FIGS. 17 to 19 and corresponding elements have been given the same reference numerals. The only difference is that, in this embodiment, the fixed blade 14a'' is formed integrally with the guide and support element, which is denoted 60 in FIGS. 20 and 21. Support element 60 is generally cylindrical and includes a longitudinal bore therein the center of which is, as shown in FIG. 21, offset from a horizontal line, as viewed in FIG. 21, through the center of a flat face of element 60 by an amount D1 and offset to the left of a corresponding vertical line, as viewed in FIG. 21, by an amount D2. In an exemplary, non-limiting embodiment, the distance, denoted D3, between the bottom of the proximal end of blade 14a″ and the center of bore 60 is 0.123 inches, the distance D1 is 0.050 inches and the distance D2 is 0.010 inches. The significance of the offset axes is discussed below.

Figure 22:
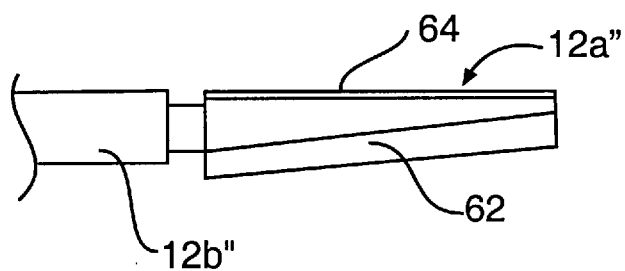
FIGS. 22, 23 and 24 are a top plan view, a side elevational view, and a front elevational view, respectively, of a further embodiment of the rotating electrode member.
Figure 23:
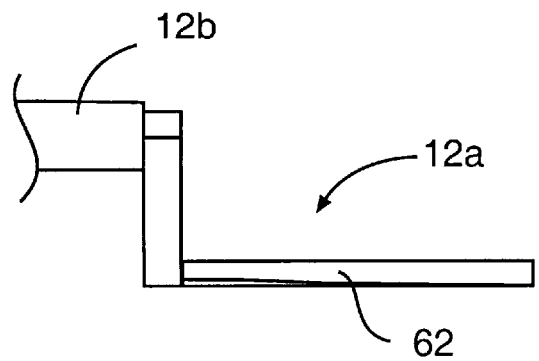
Figure 24:
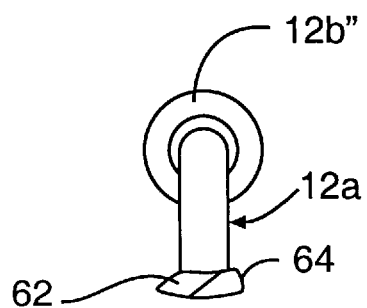

Referring to FIGS. 22 to 24, a further embodiment of the rotatory scissors blade or electrode member of the invention is shown. The overall electrode member is again similar to that of FIGS. 1 to 4 and like elements have been given the same reference numerals with double primes attached. The blade of this embodiment includes an elongate slanted cutting edge 62 and an opposed flat or blunt side or edge 64 and is specifically constructed to be used with the fixed or stationary blades of FIGS. 17 to 19 or FIGS. 20 and 21. As noted above, the stationary blades 14″ are formed as part of an inclined cylinder, whereas the rotary blade 12″ is also formed as a part of a cylinder but one which is not inclined and which thus has an axis parallel to the longitudinal axis of the device.

For both embodiments of the fixed blade 14a″, the location of the axis of rotation of the rotary blade 12a″ is that shown in FIG. 21, i.e., one which is offset from the center of the guide support 60 (or a corresponding separate guide support for the embodiment of FIGS. 17 to 19). Thus, rotation of blade 12a″ about the axis shown pushes the blade 12a″ against the stationary blade 14a″ to create pre-loading effect between the blades. Further, with this arrangement, the blades 12a″ and 14a″ contact each other along a very thin edge or line of contact and the contact is in the nature of a moving point contact wherein the point contact between the blades moves along the lengths of the blades as the rotary blades 12a″ continues its rotation. Although in the embodiment of FIGS. 22 to 24 the rotary blade is not inclined, in a further preferred embodiment, this blade is also inclined in the manner of the fixed blade of FIGS. 17 to 19 and FIGS. 20 and 21. This also produces a very clean cutting action. More generally, in many of the scissors embodiments discussed above, a strongly focussed or concentrated mechanical cutting action is produced that enables tissue to be cleanly cut. In this regard, while the invention has been described hereinbefore in terms of electrosurgical applications, i.e., applications wherein electrosurgical energy is supplied to the blades, the invention is not limited to such applications, and can be applied to purely mechanical scissors. In other words, the scissors embodiments of the invention, such as those of FIGS. 17 to 24, can also be used as a purely mechanical scissors and do not require electrosurgical power to effect cutting of tissue.

In an implementation of the invention wherein laparoscopic bipolar graspers are provided, the electrode members 12 and 14 are formed by stainless steel tubing having a diameter of, e.g., 0.064 inches and the device is adapted to fit into small, e.g., 5 mm, cannulas. Supports corresponding to support 16 are located at both the proximal and distal ends of the instruments and are, e.g., machined from ULTEM®PEI polymer (manufactured by GE Plastics). As noted above, rollers (not shown) can be fitted to the members 12 and 14 and these members can remain as round or tubular. This enables the members to glide smoothly during the relative rotational movement.

In a laparoscopic bipolar scissors implementation, the electrode blades are preferably machined from stainless steel, and can be straight or curved. A pre-loading force between the blades is provided which is preferably on the order of 5 lb.

While the invention has been described relative to embodiments using two elongate members, more than two, e.g., three, members can be employed, all of which would rotate about their respective longitudinal axes. In an advantageous embodiment, the rotational axes of two members out of the three are coincident and the end portions thereof are offset and spaced with respect to each other through the provision of independent rotation about the rotational axes.

Although the present invention has been described with respect to specific exemplary embodiments thereof, it will be understood by those skilled in the art that other variations and modifications can be effected in these exemplary embodiments without departing from the scope and spirit of the invention.

What is claimed is:

1. A bipolar electrosurgical device comprising an end effector including at least first and second elongate electrode members supported in spaced relation one beside the other, said electrode members each having a longitudinal axis; means for applying electrosurgical power to said electrode members; and handle means for causing rotation of at least said first electrode member about the longitudinal axis thereof so as to vary the spacing between at least distal end portions of said first and second electrode members, the distal end portion of said first electrode member comprising an offset portion the spacing of which from said second electrode member is variable responsive to said rotation of said first electrode member about the longitudinal axis thereof.

2. A device as claimed in claim 1 wherein said offset portion includes a portion which extends parallel to an opposed portion of said distal end of said second electrode.

3. A device as claimed in claim 1 wherein said electrode members include proximal portions supported in spaced parallel relation.

4. A device as claimed in claim 1 further comprising an electrically insulating spacer and support element having spaced openings therethrough which said electrode members extend.

5. A device as claimed in claim 4 wherein said openings have parallel longitudinal axes.

6. A device as claimed in claim 1 wherein said distal end portion of said first electrode member is rounded in cross section.

7. A device as claimed in claim 6 wherein said distal end portion of said first electrode member is substantially circular in cross section.

8. A device as claimed in claim 6 wherein said second electrode member has a substantially planar profile in cross section.

9. A device as claimed in claim 1 wherein said distal end portion of said first electrode member includes a cutting edge.

10. A device as claimed in claim 9 wherein said distal end portion of said first electrode member further includes a blunt edge substantially opposite said cutting edge.

11. A device as claimed in claim 1 wherein at least one of said electrode members is movable axially along the longitudinal axis thereof out of registration with the other of said electrode members so as to expose one of said electrode members for use as a monopolar cutting element.

12. A device as claimed in claim 1 wherein the distal end portions of both of said electrode members each include a cutting edge.

13. A device as claimed in claim 1 wherein said second electrode member is stationary and said end portion thereof comprises a blade formed from part of a cylinder inclined towards the distal end thereof and including a cutting edge, wherein said distal end portion of said first electrode member comprises a blade formed from part of a cylinder, and including a cutting edge and said rotation means includes means for rotating said first electrode member about an offset axis such that the cutting edges of said blades contact each other along a narrow line of contact.

14. A device as claimed in claim 1 wherein said second electrode member includes a hook at the distal end thereof for preventing tissue held on said second electrode member from sliding off therefrom.

15. A device as claimed in claim 1 further comprising a further, cutting member for cutting tissue held by said electrode members.

16. A device as claimed in claim 1 wherein said first electrode member is rotatable to provide coagulation of tissue held between said electrode members at two spaced coagulation zones when electrosurgical power is applied to said electrode members, and wherein said device further comprises a further cutting member disposed relative to said electrode members so as to effect cutting of tissue held by said electrode members at a zone between said coagulation zones.

17. A method for coagulating an elongate section of tissue of a patient using a electrosurgical device having an end effector comprising first and second spaced electrodes wherein at least said first electrode is rotatable, said method comprising: placing the elongate section of tissue into a space between said first and second electrodes created by rotating said first, rotatable electrode away from said second electrode; rotating said first, rotatable electrode towards said second electrode so as to engage and hold the tissue between said electrodes at a first location on the tissue; applying electrosurgical current to said electrodes so as to produce a first weld line in the tissue held between said electrodes at said first location; rotating the first rotatable electrode away from said first location so as to engage and hold the tissue between said electrodes at a second location on the tissue; applying electrosurgical current to said electrodes to create a second weld line in the tissue held between the electrodes at said second location; and cutting the tissue between said weld lines.

18. A method as claimed in claim 17 wherein said first, rotatable electrode is rotated to said second location while the second electrode is held fixed.

19. A method as claimed in claim 18 wherein said cutting is carried out by a cutting element forming part of said electrosurgical device.

20. An electrosurgical scissors device for providing cutting, and coagulation, said scissors device comprising: first and second electrode members supported in spaced relation, said first electrode member including a distal end portion and an elongate portion defining a longitudinal axis, and said distal end portion of said first electrode member being offset from said elongate portion and including a cutting edge; means for enabling electrosurgical current to be supplied to said electrode members; and handle means for causing rotation of said first electrode member about said longitudinal axis so as to vary the spacing between the distal end portion of said first electrode member and a distal end portion of said second electrode member so as to provide cutting of tissue positioned between said electrode members with said cutting edge.

21. A device as claimed in claim 20 wherein the distal end portions of both of said electrode members include cutting edges.

22. A device as claimed in claim 21 wherein said second electrode member is stationary and said distal end portion thereof comprises a blade formed from part of a cylinder inclined towards the distal end thereof and including a cutting edge, wherein said distal end portion of said first electrode member comprises a blade formed from part of a cylinder, and including a cutting edge and said rotation means includes means for rotating said first electrode member about an offset axis such that the cutting edges of said blades contact each other along a narrow line of contact.

23. A device as claimed in claim 20 wherein said distal end portion of said first electrode member includes a surface for, when juxtaposed with an opposing surface of the distal end of said second electrode member, enabling coagulation of tissue positioned between said electrode members in response to electrosurgical current being supplied to said electrode members.

24. A device as claimed in claim 20 wherein said distal end portion of said first electrode member includes a further, rounded edge opposed to said cutting edge and movable into juxtaposition with said distal end portion of said second electrode to effect coagulation of tissue positioned between said electrode members.

25. A method of coagulation and cutting of tissue using an electrosurgical device comprising first and second spaced, elongate electrode members wherein the first electrode member is rotatable about the longitudinal axis thereof so as to vary the spacing between a distal end portion thereof and a distal end portion of the second electrode member, and wherein said distal end of said first electrode member includes a cutting edge, said method comprising: positioning tissue to be coagulated and cut into a space between said electrode members; rotating said first electrode member so that a surface of said distal end portion thereof is brought into juxtaposition with an opposed surface of the distal end portion of said second electrode member; applying electrosurgical current to said electrode members to cause coagulation of a portion of the tissue between said electrode members; and further rotating said first electrode member so as to bring said cutting edge into contact with the tissue to provide cutting thereof.

26. An electrosurgical scissors device for, in use, providing cutting of tissue, said scissors device comprising: at least first and second elongate electrode members supported in spaced relation, said first and second electrode members each including a distal end portion and an elongate portion defining a longitudinal axis, the distal end portion of one said electrode members being offset axially with respect to the longitudinal axis of the elongate portion thereof; and said distal end portion of each of said first and second members including a cutting edge; means for enabling axial movement of at least one of said first and second electrode members between a first, scissors configuration wherein the distal end portions of said electrode members are in registration within another and a second, single element cutting configuration wherein the distal end portions of said electrode members are out of registration so that one of said cutting edges is exposed for use as a monopolar cutting element; means for enabling electrosurgical current to be supplied to said electrode members; and handle means for causing rotation of said first member about the longitudinal axis thereof in the scissors configuration of said device so as to vary the spacing between the distal end portion of said first electrode member and the distal end portion of said second electrode member so as to provide cutting of tissue positioned between said first and second members with the cutting edges of said electrode members.

27. A device as claimed in claim 16 wherein said distal end portion of said first electrode member includes a surface for, when juxtaposed with an opposing surface of the distal end of said second electrode member, enabling coagulation of tissue positioned between said members in response to electrosurgical current being supplied to said electrode members.

28. An elongate rotary surgical scissors device for, in use, providing cutting of patient tissue, said scissors device having a central longitudinal axis and comprising: first and second elongate members supported in spaced relation, said first member including a distal end portion including a cutting edge and an elongate portion connected to said distal end portion and defining a further longitudinal axis offset from said central longitudinal axis, and said second member including a distal end portion; and means for rotating said first member about said further longitudinal axis so as to provide relative movement between the distal end portion of said first member and the distal end portion of said second member to a closed position so as to provide cutting of patient tissue positioned between said members with said cutting edge.

29. A device as claimed in claim 28 wherein the distal end portion of said second member includes a cutting edge.

30. A device as claimed in claim 29 wherein said second member is stationary and said distal end portion thereof comprises a blade formed from part of a cylinder inclined towards the distal end thereof and including the cutting edge of the second member.

31. A device as claimed in claim 30 wherein said second member comprises an elongate cylindrical portion having a longitudinal axis coincident with said central longitudinal axis and having an outer peripheral surface, said blade being connected to said cylindrical portion, being offset radially from said second longitudinal axis and including a base part coextensive with said outer peripheral surface.

32. A device as claimed in claim 30 wherein said distal end portion of said first member comprises a further blade formed from part of a cylinder and including the cutting edge of the first member.

33. A device as claimed in claim 32 wherein said further longitudinal axis is offset from said central longitudinal axis such that the cutting edges of said blades contact each other along a narrow line of contact.

34. A rotary surgical scissors device for, in use, providing cutting of patient tissue, said scissors device having a central longitudinal axis and comprising: first and second members supported in spaced relation, said first member including a distal end portion and a further, offset portion connected to said distal end portion and defining a further longitudinal axis, said second member including a base portion and a distal end portion affixed to said base portion and spaced radially from said central longitudinal axis an amount defining an outer limit of an outer peripheral boundary of the device, and said distal end portions of said first and second members each including a cutting edge; and means for rotating said first member about said further longitudinal axis so as to vary the relative positions of the distal end portions of said first and second members between a closed position wherein said cutting edges provide cutting and an open position, said central longitudinal axis and said further longitudinal axis being offset such that said distal end portion of said first member is disposed within said outer peripheral boundary in said closed position and is disposed outside of said outer peripheral boundary in said open position.

35. A device as claimed in claim 34 wherein said further longitudinal axis is offset from said central longitudinal axis in a first coordinate direction as well as in a second, orthogonal coordinate direction.

36. A device as claimed in claim 34 wherein said base portion of said member includes an outer cylindrical surface defining said outer peripheral boundary of said device.

37. A device as claimed in claim 34 wherein said second member is stationary and said distal end portion thereof comprises a blade formed from part of a cylinder inclined towards the distal end thereof and including the cutting edge of the second member.

38. A device as claimed in claim 37 wherein said base portion of said second member comprises a cylindrical element having a longitudinal axis coincident with said central longitudinal axis and having an outer peripheral surface defining said outer peripheral boundary of said device, and said blade being connected to said cylindrical element and including a base part coextensive with said outer peripheral surface.

39. A device as claimed in claim 37 wherein said distal end portion of said first member comprises a further blade formed from part of a cylinder and including the cutting edge of said first member.

40. A device as claimed in claim 39 wherein said further longitudinal axis is offset from said central longitudinal axis such that the cutting edges of said blades contact each other along a narrow line of contact.

41. A surgical scissors device for, in use, providing cutting of patient tissue, said scissors device comprising: at least first and second elongate cutting members supported in spaced relation, said first and second members each including a distal end portion and an elongate portion defining a longitudinal axis, and said distal end potion of each of said first and second members including a cutting edge; means for enabling axial movement of at least one of said first and second members between a first, scissors configuration wherein the distal end portions of said members are in registration within another and a second, single element cutting configuration wherein the distal end portions of said members are out of registration so that one of said cutting edges is exposed for cutting; and means for rotating said first member about the longitudinal axis thereof in the scissors configuration of said device so as to vary the spacing between the distal end portion of said first member and the distal end portion of said second member so as to provide cutting of tissue positioned between said first and second members with the cutting edges of said members.

42. An elongate rotary surgical device for, in use, providing engagement of patient tissue, said device having a central longitudinal axis and comprising: first and second elongate members supported in spaced relation, said first member including a distal end portion and an elongate portion connected to said distal end portion and defining a further longitudinal axis offset from said central longitudinal axis, and said second member including a distal end portion; and handle means for rotating said first member about said further longitudinal axis so as to provide relative movement between the distal end portion of said first member and the distal end portion of said second member to a closed position so as to provide engagement of patient tissue positioned between said members.

43. A device as claimed in claim 42 wherein said second member is stationary and said distal end portion thereof is formed from part of a cylinder inclined towards the distal end thereof.

44. A device as claimed in claim 43 wherein said second member comprises an elongate cylindrical portion having a longitudinal axis coincident with said central longitudinal axis and having an outer peripheral surface, said distal end portion of said second member being connected to said cylindrical portion, being offset radially from said second longitudinal axis and including a base part coextensive with said outer peripheral surface.

45. A device is claimed in claim 42 further comprising means for supplying electrosurgical power to said members to provide coagulation of tissue held in an engagement between said members.

* * * * *